United States Patent [19]

Cole

[11] 4,049,828

[45] Sept. 20, 1977

[54] INSECTICIDAL AND INSECT-REPELLANT METHODS AND COMPOSITIONS

[76] Inventor: Larry K. Cole, 2709 Judith Drive, Champaign, Ill. 61820

[21] Appl. No.: 595,277

[22] Filed: July 14, 1975

Related U.S. Application Data

[63] Continuation-in-part of Ser. No. 494,540, Aug. 5, 1974, abandoned.

[51] Int. Cl.$^2$ .............................................. A01N 9/24
[52] U.S. Cl. ................................................... 424/333
[58] Field of Search ....................................... 424/333

[56] References Cited

U.S. PATENT DOCUMENTS

| | | | |
|---|---|---|---|
| 3,595,975 | 7/1971 | Gauvreau | 424/263 |
| 3,637,859 | 1/1972 | Blumenthal | 424/333 |

FOREIGN PATENT DOCUMENTS

| | | | |
|---|---|---|---|
| 2,534,765 | 2/1976 | Germany | 424/333 |

OTHER PUBLICATIONS

Chem. Abst. 75 16547(t)(71) "Antimicrobial... citral'-'—Stevens et al.
"Insect Juvenile Hormone Analogues" K. SIA'MA -1079, 1096, 1097- 1971.
Chem. Abst. 75 101,300(b)(71) "Disinfecting Compositions" Gauvreau.
Chem. Abst. 76 6635(b)(72) "Perfumes—Crotonate" Exner et al.
Chem. Abst. 79 57561(u)(73) "Antiseptic—Chemicals" Schweisheimer.

*Primary Examiner*—Albert T. Meyers
*Assistant Examiner*—D. W. Robinson
*Attorney, Agent, or Firm*—Mason, Kolehmainen, Rathburn & Wyss

[57] ABSTRACT

Citral is an effective insecticide, nematocide, and insect-repellant. At 1 ppm. it kills 100% of adult moths in two hours. At 0.2% concentration in housefly growth media, it prevents flies from laying eggs. At 0.02% concentration in soil, it reduces the nematode population 99.5%.

6 Claims, No Drawings

INSECTICIDAL AND INSECT-REPELLANT METHODS AND COMPOSITIONS

CROSS-REFERENCE TO RELATED APPLICATIONS

This application is a continuation-in-part of Serial No. 494,540 filed August 5, 1974, now abandoned.

This invention relates to insecticidal and insect-repellant methods and compositions. More particularly, it relates to insecticidal methods and compositions based on citral.

Citral is an aldehyde which occurs in the volatile oils of lemon, lemon grass and orange. It is used in perfumery and as an intermediate in the synthesis of vitamin A. Its insecticidal properties have previously been unknown.

GENERAL DESCRIPTION OF INVENTION

In accordance with this invention, it has been discovered that citral has powerful pesticide and pest-repellant properties. It is toxic and/or repellant to insects of the orders Lepidoptera and Diptera and to worms of the class Nematoda. These orders include moths, butterflies, flies, mosquitoes and gnats.

The vapors of citral are very toxic to insects such as the almond moth, *Cadra cautella*, and toxic to four-day-old female houseflies. Citral also completely inhibits the development of adult flies from eggs.

A concentration of citral of 1 milligram per liter of air (1 mg/l) produced 100% kill of adult moths within two hours in a closed environment at 24°–26° C. The $LC_{99} = 1$ ppm. (parts per million). The same concentration is effective against the Indian meal moth, *Plodia interpunctella*.

Houseflies, *Musca domestica*, will not lay a single egg in simulated cow dung containing 0.2% of citral, whereas 3000 to 6000 eggs are routinely layed in the controls. As a fumigant, citral has an $LC_{99} = 20$ ppm. after 24 hours at 24°–26° C.

Citral causes the silk worm, *Bombyx mori*, to regurgitate within two minutes after topical application as little as 0.03 microliter per larva. Citral at 0.1 microliter per larva completely inhibits the feeding of *B. mori* and the larvae slowly die.

A single application of 50 ml of an 0.1% aqueous citral solution to 250 g. of soil initially containing 50 nematodes, *Rotylenchulus reniformis*, per 100 ml. of soil, reduced the nematode count from 61 nematodes per 100 ml of soil to 0.3 nematode per 100 ml. of soil at the end of 70 days.

Against housefly larvae, the lethal concentration of citral in simulated cow dung resulting in 58% larval mortality was 0.4%.

Against mosquitoes, third instar larvae of *Culex pipiens*, aqueous citral solutions of concentration of 167 ppm. and 333 ppm. produced 100% kill of the larvae after 24 hours exposure.

The median lethal dose of topically applied citral to 4-day-old adult female houseflies is 1850 micrograms per gram of body weight.

Citral at a concentration of 1.6% by weight of simulated cow dung completely inhibits the development of adult houseflies from eggs. No eggs were oviposited in simulated cow dung containing 0.2% by weight of citral.

DETAILED DESCRIPTION OF INVENTION

The houseflies represented a wild strain collected in Athens, Geo. Larvae were reared on CSMA-media (Ralston Purina Company, St. Louis, Missouri), a standard housefly rearing medium. Colonies were maintained at 26± 2° C, at a relative humidity of 70 ± 5%. Adult food consisted of sucrose mixed with dry milk; water bottles with cotton wicks were provided. Batches of adults, topically treated with a test solution, were subsequently maintained in cardboard cups with screen tops, each with a vial of 5% sucrose in water.

Various concentrations of citral in acetone were topically applied to 4-day old adult females after anesthetizing them with $CO_2$. Several initial tests were conducted in order to determine the approximate dosage range that was effective. One microliter of solution was applied to the pronotum using a microapplicator. Forty female flies were used in each treatment; controls were those flies treated with 1 microliter acetone containing no citral. The number of dead flies was recorded 24 hours after treatment.

As shown in Table 1, the $LD_{50}$ of topically applied citral in acetone to 4-day-old adult female houseflies was approximately 1,850 micrograms per gram of body weight. Compared to commercial insecticides, this is a very high dosage, indicating that citral is weakly toxic to houseflies, if applied as a contact insecticide.

TABLE 1

| | Data for the topical median lethal dose of citral in acetone to adult female houseflies | | | |
|---|---|---|---|---|
| Total Flies | Alive | Dead | Corrected* % Kill | Dosage microgram/gram |
| 40 | 36 | 4 | 0 | 0 |
| 40 | 32 | 8 | 11 | 1,590 |
| 40 | 28 | 12 | 22 | 1,720 |
| 40 | 25 | 15 | 31 | 1,840 |
| 40 | 5 | 35 | 86 | 1,960 |
| 40 | 1 | 39 | 97 | 2,210 |

Average weight determined from 360 female houseflies = 18.1 mg per fly.
*Corrected % Kill = $\frac{\text{alive in control} - \text{alive in treatment}}{\text{alive in control}} \times 100$

Development of Houseflies in Media Containing Citral

Fungus readily develops in housefly media within 24 hours, and often the whole surface is covered with fungus within 2 days. It has been established that citral is fungitoxic (Cole application filed July 22, 1974) and only weakly toxic to adult houseflies. Therefore, if the fungus impaired the development of the flies, it seems possible that the addition of citral to the media might improve the growth of the insect, instead of inhibiting it.

| Formulation of the Media | | | | |
|---|---|---|---|---|
| Volume of Citral, ml | Tap Water, ml | 20% NaOH, ml | Yeast q | CSMA Medium q |
| 18.6 | 681 | 10 | 2.2 | 451.5 |
| 9.3 | 691 | 10 | 2.2 | 451.5 |
| 4.7 | 695 | 10 | 2.2 | 451.5 |
| 2.3 | 698 | 10 | 2.2 | 451.5 |
| 1.2 | 699 | 10 | 2.2 | 451.5 |
| 0.0 | 700 | 10 | 2.2 | 451.5 |

The indicated volume of citral was added to the indicated volume of water in a large flask and mixed by shaking; NaOH was added and mixed, followed by the yeast. This mixture was transferred to a small stainless steel tub and the indicated amount of dry CSMA media added and mixed. From each batch of media containing a given concentration of citral, three replicate containers were prepared; 275 g of media was placed in each of three-quart jars.

Housefly eggs were collected over an eight-hour period from two cages of adult 8-day-old flies. Fifty eggs resting on paper were placed in each quart jar, and the jars sealed with paper towels. Eggs were added on the day the media was prepared. The number that hatched was determined 32 hours later, and the number of adults, 12 days later.

Results demonstrated that citral was detrimental to the development of both the houseflies and the fungus. At the end of 32 hours, the surface of the medium in each of the three control jars (those containing no citral) was covered with a white fluffy fungus; it had not penetrated the paper on which the eggs were resting. However, there was no visible fungal growth in any of the fifteen jars containing citral.

Citral was also detrimental to the development of houseflies (Table 2). The first instar larvae appeared more susceptible to the toxic effects of citral than did the eggs. For example, at 0.4% citral per weight of medium, 30% of the eggs were killed, whereas 58% of the young larvae were killed. At 1.6% citral per weight of medium, all of the young larvae were killed, but only 54% of the eggs were killed. However, the present experiment cannot clearly differentiate the developmental stage most susceptible to the toxic effects of citral. Since young larvae developed from treated eggs, the apparent greater susceptibility of first instar larvae as compared to eggs, may simply be a reflection of an accumulated toxic effect, as opposed to real differences in the susceptibility of the different developmental stages.

Insect Repellant Characteristics of Citral

The previous experiment was conducted in an insectary in which there were loose, or free flying, phorid flies (humpbacked flies) which are usually undesirable; however, in this case they are beneficial. The paper towels that covered the control jars, in which the houseflies were being reared, were blanketed with phorids. Evidently they were attracted by the strong odor of the housefly media. However, none of these flies were on the covers of the 15 experimental jars which contained citral. This observation was followed by the demonstration that houseflies will not lay eggs in a medium containing citral.

TABLE 2

Development of houseflies in media containing citral

| % Citral in medium | % Mortality of eggs after 32 hrs. | % Kill of 1st instar larvae from surviving eggs after 32 hrs. | Number of live adults after 12 days | Total % mortality after 12 days based on adult emergence |
|---|---|---|---|---|
| 0 | 7 | 0 | 104 | 31 |
| 0.1 | 11 | 1.5 | 120 | 20 |
| 0.2 | 17 | 8 | 100 | 33 |
| 0.4 | 30 | 58 | 39 | 74 |
| 0.8 | 35 | 57 | 10 | 93 |
| 1.6 | 54 | 100 | 0 | 100 |

A routine method used to collect housefly eggs is to use a container, such as a paper cup, about half full of aged, and moist larval medium. The cup is covered with a piece of black cloth, or paper toweling, and this is indented so that it touches the moist medium. The females are readily attracted to this oviposition site. This type of design was used in order to determine the ovipositional behavior of houseflies in the presence of citral.

Aged fly medium was made to contain various concentrations of citral, and placed in an oviposition cup as described above; the medium in the control cups did not contain citral. In one set of experiments, two cups were placed in an individual cage; one contained a given concentration of citral and one contained none. In a second set of experiments, only a cup containing a given concentration of citral was added to the cage; that is, no alternative ovipositional site free of citral was offered to the flies. All cages contained 100 or more adult flies. The cups were examined for eggs after having been in the cages for 24 hours.

It was found that no eggs were layed in those cups containing at least 0.2%, or more of citral, whereas those control cups placed beside the test cups routinely contained from 3,000 to 6,000 eggs. Flies did not lay eggs in a cup containing 0.2% or more citral, even if it was the only cup added to the cage.

Toxicity of Citral Vapors Against Cadra cautella

The almond moth, *Cadra cautella* (Walker), is one of several economically important pests of stored agricultural products. It feeds on more than twenty different foods including peanuts and almonds. The results indicate that citral may be an effective control chemical against this pest.

In the first set of experiments, substrates which could absorb or adsorb the vapors of citral were not added to the test chambers; thus, the surface to volume ratio was low. With a microsyringe, a measured volume of citral (neat) was placed on the metal lid of a 500-ml jar containing ten newly emerged female moths. A screen wire partition within the jar prevented the moths from coming into direct contact with the liquid chemical when the inverted jar was twisted into position within the rim of the lid.

In the second set of experiments, 500 g of rearing media (mostly cereals, honey, and glycerine) were added to each gallon container in order to increase the surface area to volume ratio within the test container. To obtain the desired concentrations of citral within each container, a suspension of citral in water was aspirated onto the medium within the test jar as the jar was agitated to facilitate maximum exposure of the medium to the citral. The volume of citral added to the media is given below, along with an equivalent method of expressing the resulting concentrations.

| Volume of Citral in Gallon Jar Containing 500 g of Medium | | | | |
|---|---|---|---|---|
| 0 | 0.05 ml | 0.1 ml | 0.2 ml | 0.4 ml |
| Above values expressed as mg of citral per liter of space | | | | |
| 0 | 13 | 26 | 52 | 104 |

Newly emerged moths, 20 males plus 20 females, were introduced into each container one hour after adding the citral, and the metal lids were replaced on the containers.

In all experiments, three replications of each concentration were used, and all experiments were conducted at room temperature, 24°–26° C.

The results clearly indicate that citral vapors are toxic at a low concentration against the almond moth (Table 3). All concentration initially produced excitement, or hormesis. Subsequently, the moths became uncoordinated and immobile at the indicated knock-down time. Those moths exposed to 0.2 and 0.6 mg/1 of citral completely recovered within 24 hours. The test containers were not completely air-tight, and it appears that the chemical dissipated from the containers, allowing the moths to recover. The concentration of citral required for 100% kill of *Cadra cautella* in a closed environment devoid of medium was 1 mg/1 (or 1 ppm).

TABLE 3

Fumigant effects of citral on the Almond Moth

| Citral mg/1 | Knock-down time, minutes | Number of Newly Emerged Females | % Kill at 2 hrs. |
|---|---|---|---|
| 0.2 | 25–30 | 10 | 0 |
| 0.6 | 25–30 | 10 | 0 |
| 1.0 | 15–20 | 10 | 100% |
| 2.0 | 15–20 | 10 | 100% |

In the second set of experiments, the surface area to volume ratio was substantially greater than that used in the earlier experiments, and there was a substantial difference in the concentration of citral required for 100% kill. In closed gallon jars, containing 500 g of medium each, the concentration of citral required for 100% kill of *C. cautella* was 52 mg/1, as compared to 1 mg/1 in jars devoid of medium. Thus, the above clearly indicates that if citral were to be used in an applied manner, such as a fumigant in a warehouse, the existing surface area to volume ratio would be an important consideration in predicting its effective insecticidal concentration.

Citral also possesses fungitoxic properties. Thus, if citral were applied to control an insect pest, that portion of the chemical absorbed by the surrounding medium would not necessarily be wasted if that medium, such as peanuts, were also subject to fungal pests. Furthermore, since citral has a low boiling point, its removal, if necessary, from a stored agricultural product would probably not be difficult.

I claim:

1. A method of killing dipterous and lepidopterous insects which comprises applying to said insects or habitat thereof citral vapors at concentrations of about 1 to 20 ppm. in air.

2. A method of inhibiting the development of house flies which comprises applying to the eggs or larvae thereof a growth-inhibiting amount of citral by adding the citral to a concentration of about 0.4% in the medium in which the eggs or larvae are living.

3. A method of inhibiting the oviposition of adult female house flies which comprises applying an amount of citral sufficient to repel the flies, to a concentration of about 0.2%, to the medium eliciting the ovipositional response.

4. A method of inhibiting the feeding of the larvae of moths which comprises applying to the larvae 0.03 to 0.1 microliter of citral per larva.

5. A method of killing the larve of mosquitoes which comprises adding a lethal amount of citral to the water in which they are living.

6. A method of killing plant pathogenic nematodes which comprises applying citral to the nematodes at a concentration of about 0.2% in the soil surrounding the nematodes.

* * * * *